United States Patent [19]

Barthomeuf

[11] Patent Number: 4,584,424
[45] Date of Patent: Apr. 22, 1986

[54] PROCESS FOR SEPARATING ETHYLBENZENE FROM XYLENES BY SELECTIVE ADSORPTION ON A BETA ZEOLITE

[75] Inventor: Denise M. Barthomeuf, Lyon, France

[73] Assignee: Exxon Research & Engineering Company, Florham Park, N.J.

[21] Appl. No.: 666,196

[22] Filed: Oct. 29, 1984

[51] Int. Cl.$^4$ .......................... C10G 25/03; C07C 7/13
[52] U.S. Cl. .................................. 585/828; 208/310 Z
[58] Field of Search ..................... 208/310 Z; 585/828

[56] References Cited

U.S. PATENT DOCUMENTS

| | | | |
|---|---|---|---|
| 3,308,069 | 3/1967 | Wadlinger et al. | 502/62 |
| 3,686,342 | 8/1972 | Neuzil | 208/310 Z X |
| 3,793,385 | 2/1974 | Bond et al. | 208/310 Z |
| 3,864,416 | 2/1975 | Campbell et al. | 208/310 Z X |
| 3,894,109 | 7/1975 | Rosback | 208/310 Z X |

FOREIGN PATENT DOCUMENTS

| | | | |
|---|---|---|---|
| 0037129 | 11/1979 | Japan | 585/828 |
| 1330956 | 9/1973 | United Kingdom | 585/828 |

*Primary Examiner*—John Doll
*Assistant Examiner*—Glenn A. Caldarola
*Attorney, Agent, or Firm*—E. Thomas Wheelock

[57] ABSTRACT

The invention relates to a process for selectively adsorbing ethylbenzene from a stream containing one or more isomeric xylenes. The ethylbenzene is adsorbed on a Beta zeolite. Certain desorbents, of which para-diethylbenzene is preferred, give the zeolite good ethylbenzene selectively over the xylenes.

22 Claims, No Drawings

PROCESS FOR SEPARATING ETHYLBENZENE FROM XYLENES BY SELECTIVE ADSORPTION ON A BETA ZEOLITE

FIELD OF THE INVENTION

This invention relates to a process for selectively separating ethylbenzene from a feedstream containing one or more isomeric xylenes by using a Beta zeolite and one or more of a group of organic desorbents. The preferred desorbents are monosubstituted benzenes where the substituent contains a heteroatom, monoalkylbenzenes, and paradialkylbenzenes.

BACKGROUND OF THE INVENTION

Some crystalline aluminosilicates, or zeolites, are useful as adsorbents in separating a particular hydrocarbon compound from mixtures of hydrocarbons containing the compound. In particular, zeolites are widely used for selective separation of paraxylenes from mixtures containing other $C_8$ aromatic compounds such as metaxylene, orthoxylene, or ethylbenzene. For example, U.S. Pat. Nos. 3,636,121; 3,686,342; 3,686,343; 3,835,043; 3,855,333; 3,878,127; 3,894,108; 3,903,187 and 4,265,788 are all directed towards methods of removing paraxylene from mixtures or of selectively separating paraxylene and ethylbenzene from mixtures containing other components, using various types of zeolites as adsorbents. Paraxylene is a commerically important aromatic hydrocarbon isomer since its use in the manufacture of terephthalic acid is a critical step in the subsequent production of various fibers such as Dacron.

This invention, however, relates to a process for separating ethylbenzene from a feed mixture containing ethylbenzene and at least one other xylene isomer and is therefore unrelated to paraxylene separation processes. Additionally, in the process disclosed herein, ethylbenzene is selectively adsorbed in relation to the less selectively adsorbed xylene isomers.

While a separation of paraxylene from other xylene isomers is desirable in certain circumstances, it has become increasingly desirable to recover ethylbenzene from streams containing both ethylbenzene and xylene isomers. Ethylbenzene has great commerical importance since it is a building block in the production of styrene further, the cost of producing ethylbenzene by the reaction of benzene with ethylene has steadily increased. These costs have prompted research efforts in the recovery of ethylbenzene from various $C_8$ aromatic feedstreams which already contain ethylbenzene. Such feedstreams may be $C_8$ aromatic extracts resulting from various solvent extraction processes, from pyrolysis gasoline, or from reformed naphtha.

It is known that zeolite Beta has been used to adsorb mixture of paraxylene and ethylbenzene selectively from mixtures comprising ethylbenzene, orthoxylene, metaxylene and paraxylene using toluene as a desorbent. See U.S. Pat. No. 3,793,385 to Bond et al, issued Feb. 19, 1974. Bond et al additionally suggests a large number of cations including Li, K, Cs, Mg, Ca, Sr, B La and Ce may be included in the zeolite. Cs and K are especially preferred.

However, the invention disclosed herein is based on the discovery that certain desorbents modify the behavior of zeolite Beta so that is adsorbs ethylbenzene in substantial preference to paraxylene and the other isomeric xylenes. Generically, these desorbents belong either to the family of monosubstituted benzenes wherein the substituent contains a hereoatom selected from the group consisting of O, S, P, and the halogens (particularly halobenzenes, for instance, iodobenzene) and alkylbenzenes with a linear side chain or to the family of para-dialkylbenzenes (particularly, p-diethylbenzene and p-methyl n-propylbenzene).

Other zeolite systems are known which selectively adsorb ethylbenzene from mixed $C_8$ aromatic streams in the presence of diethylbenzene as desorbent. One such process is disclosed in U.S. Pat. No. 3,943,182 to Neuzil et al, issued Mar. 9, 1976. However, the zeolites disclosed therein are either Type X or Type Y. The adsorptive activity of a particular type of zeolite is not easily predictable, if it is predictable at all. Indeed, the direction in which zeolite selectivity is affected by a particular desorbent is even less predictable.

SUMMARY OF THE INVENTION

The invention disclosed herein is directed to a process for selectively adsorbing ethylbenzene from feedstreams containing both ethylbenzene and mixtures of xylenes. The process utilizes Beta zeolites and certain desorbents. The desorbents may be generically described as monoalkylbenzenes, paradialkylbenzenes and mono-substituted benzenes having a heteroatom selected from the group consisting of O, S, P and the halogens in the substituent group. This combination of desorbent and zeolite provides simultaneously acceptable values for the selectivities of ethylbenzene as compared to paraxylene, metaxylene, or orthoxylene. These desorbents are unique in that they increase each ethylbenzene selectivity factor with respect to the exylene isomers.

Ethylbenzene can be separated and recovered from a feedstream mixture containing at least one and preferably all isomeric xylenes by the process made up of (a) contacting the hydrocarbon mixture with a Beta zeolite, so that the contacting takes place under conditions to affect a selective adsorption of ethylbenzene by the zeolite, (b) passing through the zeolite, during or after the contacting step, a desorbent which produces a selectivity factor ($\alpha$EB/xylene) for each xylene which is greater than about 2 under the same conditions, and which has a desorbent strength factor ($\alpha$EB/desorbent) in the range of 0.1 to 10, and (c) recovering from the zeolite a stream enhanced in the concentration of ethylbenzene relative to the isomeric xylenes.

The selectivity factor, which represents the selectivity of the adsorbent for ethylbenzene over a particular xylene, is defined by the expression:

$$\alpha\text{EB/xylene isomer} = \frac{\text{amount of ethylbenzene in zeolite}}{\text{amount of ethylbenzene in non-adsorbed phase}} \times \frac{\text{amount of xylene isomer in non-adsorbed phase}}{\text{amount of xylene isomer in zeolite}}$$

The desorbent strength factor, which represents the selectivity of the adsorbent for ethylbenzene over the desorbent, is defined by the expression:

$$\alpha\text{EB/desorbent} = \frac{\text{amount of ethylbenzene in zeolite}}{\text{amount of ethylbenzene in non-adsorbed phase}} \times$$

$$\frac{\text{amount of desorbent in non-adsorbed phase}}{\text{amount of desorbent zeolite}}$$

DESCRIPTION OF THE PREFERRED EMBODIMENT

The feedstream mixtures which are applicable to the present invention comprise at least ethylbenzene and one xylene isomer. Preferably the feedstream contains ethylbenzene and all of the xylene isomers. In addition, the feedstream mixture may contain up to about 20%, preferably less than about 10 volume percent, of non-aromatic components such as paraffins, cycloaliphatic or olefinic compounds. Such components will tend to be adsorbed by the zeolite in smaller amounts than the aromatic components. Whatever else may be present in the mixture however, the process embodies the technique of separating ethylbenzene from various xylenes.

Feedstream mixtures containing $C_8$ aromatics such as ethylbenzene and xylene isomers are generally obtained via such processes as reforming, pyrolysis and isomerization. The paraxylene isomer is often extracted from this mixture by the processes of crystallization, extraction, or selective adsorption, thus leaving a feedstream relatively rich in ethylbenzene and metaxylene and substantially depleted in paraxylene. The process steps described herein as part of the invention may be used after such a paraxylene separation process or preferably may be used before such a process. The latter method improves the efficiency of the overall process since the paraxylene recovered should then have a higher purity with no ethylbenzene impurity.

In the process described herein, the ethylbenzene is separated from the xylene isomers in the feedstream mixture by contacting the mixture with the zeolite adsorbent defined below in such manner that the ethylbenzene is more selectively adsorbed than the xylene isomers. Concurrently with this contacting step, or subsequent thereto (if the operation is a batch operation), desorbents are passed through zeolites so as to desorb the enriched ethylbenzene containing phase formed adsorbed on the zeolite.

The zeolite contacting step may be conducted in a batch or continuous mode of operation. For example, the adsorbent may be placed in a fixed bed which is intimately contacted with a feedstream mixture containing ethylbenzene and xylene along with a desorbent or it may be placed in a fluidized bed which is contacted with a mixture and a desorbent in a continuous operation. The fluidized bed may be used with or without magnetic stabilization and with or without real or simulated co- or countercurrent flows. Where the adsorbent is employed in a static bed, the process may be semicontinuous, e.g., or operated as a pulsed chromatographic process. The adsorbent may be placed in a set of two or more static beds such that the feedstream mixture is contacted with one bed while the desorbent is passed through one of the others. In some instances, it may be desirable to remove a leastadsorbed component from the voids in a bed by flushing with a very weakly adsorbed material, e.g., a paraffin, before recovery of ethylbenzene by addition of the desorbent. Moving or simulated moving beds represent a preferred mode of operation because of the greater efficiency in the resulting separation.

Temperatures for contacting and desorption steps of the process herein may vary broadly depending, inter alia, on the desorbent used, but generally will range from about room temperature to about 300° C. Similarly operating pressures will vary considerably but generally will range from about atmospheric to about 30 atmospheres (3 megapascals) pressure.

The desorbent employed in the present invention may be defined as a compound which is characterized by its minimum ability to enhance the selectivity of Beta zeolites in separating ethylbenzene from xylene isomers and by maintaining those selectivities above about 2.0. The selectivity is expressed herein as a selectivity factor, designated $\alpha$EB/xylene isomer, which is defined above. The value of the selectivity factors should be as high as possible. Too low a factor will result in poor separation between two components.

Another parameter which characterizes the desorbent herein is the strength of the desorbent, which is expressed by a desorbent strength factor, designated $\alpha$EB/desorbent as defined above. This factor represents the ratio of the adsorption strength of the zeolite for the ethylbenzene to the adsorption strength of the zeolite for the desorbent. If the desorbent is too strongly adsorbed relative to the ethylbenzene, i.e., so that the desorbent strength factor is less than 0.1, then both ethylbenzene and the xylenes will be eluted at a similar time. On the other hand, a desorbent having a desorbent strength factor of greater than about 10 will not compete favorably with the ethylbenzene, necessitating large volumes of desorbent to recover all the ethylbenzene. The ethylbenzene thus collected would be contained in a large amount of desorbent so that an expensive and energyconsuming distillation procedure would be required to recover the ethylbenzene. The desorbent strength factor ratio is preferably in the region of about 1 to about 2, but for the purposes herein is generally in the range from about 0.1 to about 10.

The desorbents applicable to the disclosed process may be generically described as monoalkylbenzenes, paradialkylbenzenes and monosubstituted benzenes having a heteroatom substituted in the ring.

The alkyl substituent of the monoalkylbenzene preferably contains three to twelve carbon atoms. Especially preferred are those compounds belonging to the group consisting of n-butylbenzene, n-pentylbenzene, n-heptylbenzene, n-nonylbenzene and dodecylbenzene. Most preferred of this group is n-nonylbenzene. In addition, mixtures of two or more desorbents which have the requisite characteristics may also be employed as desorbents desired. The desorbent may be diluted with a liquid inert material such as a paraffin or a cycloparaffin.

Another class of desorbents producing excellent ethylbenzene selectivity on Beta zeolites is made up of the paradialkylbenzenes. The alkyl chains may be of any convenient length. Preferably the alkyl moieties are fairly short chains, i.e., less than five carbon atoms. Especially preferred compounds include p-diethylbenzene and paramethyl-n-propylbenzene. Again, these compounds may be used as mixtures either with other paradialkylbenzenes, monosubstituted benzenes or inert diluents such as paraffins, cycloparaffins or olefins.

Monosubstituted benzenes having a heteroatom in the substituent group are also quite useful in this invention. The heteroatom should be selected from the group consistng of S, O, P, and the halogens. Especially preferred are the monohalobenzenes particularly iodobenzene.

The zeolite Beta has a poorly understood structure. However, U.S. Pat. No. 3,308,069 (which is incorporated by reference) describes the preparation of the zeolite. Bond et al, discussed above, additionally describes methods for producing the zeolite and for exchanging the zeolites with various alkali and alkaline earth metal cations. An integral portion of this invention involves use of Beta zeolites containing at least one cation selected from the group consisting of alkali and alkaline earth metals and mixtures thereof. I have found that the selectivity of zeolite Beta increases with the size of the substituent cations. Consequently, rubidium substituted Beta provides better selectivity than does potassium and cesium substituted Beta is even better still. Zeolite Beta substituted with potassium gives better selectivity than do those substituted with sodium.

By zeolite Beta is meant the zeolite having as its structure that disclosed in U.S. Pat. No. 3,793,385. The zeolite may also have any atomic Si/Al and the framework may have other atoms such as Ga, B, Ge or P substituted therein. The positive charges of the zeolitic framework must be substantially neutralized by one or more types of cations.

After the feedstream mixture and desorbent have been contacted with the zeolite, the respective eluted product streams containing the various components are directed to separate recovery vessels. The stream which is enhanced in ethylbenzene content due to the separation achieved by the adsorption and desorption operations, may be further processed to recover the ethylbenzene by, e.g., distillation, or other suitable recovery techniques.

The following examples further illustrate the efficacy of the present invention and in these examples all parts or percentages are given by weight and all temperatures are in degrees Centigrade unless otherwise indicated.

EXAMPLE 1

Beta zeolite was produced in the presence of excess tetraethylammonium hydroxide using the procedure outlined in U.S. Pat. No. 3,308,069. The starting zeolite had an atomic Si/Al ratio of 13.3 and contained (weight %) $SiO_2$—94.71%, $Al_2O_3$=6.0%, Na=0.37%, K=500 ppm and N=1.6%. About 90% of the cations saturating the framework negative charges were tetraethylammonium and there were excess ions trapped in the cages. The zeolite was then calcined at about 500° C. for more than 15 hours to remove the organic cations. Other methods of removing the template organic cations would, of course, be acceptable. Separate portions of the cationated zeolite were then exchanged with chloride solutions of the various alkaline cations, dried, exchanged at room temperature, dried, exchanged at room temperature, washed and dried again. The exchanged zeolites were then dehydrated in a 550° C. oven flushed with dry nitrogen for at least 15 hours.

About three hundred milligram samples of the dried zeolite were transferred each to a series of 2-ml vials sealed with a septum cap. To each bottle was added, by syringe, the respective feed in an amount representing the capacity of the zeolite. The vials were agitated at room temperature for 2 to 24 hours under ambient conditions to reach adsorption equilibrium. The vapor phase above the zeolite was analyzed by gas chromatograph. Due to the selectivity of adsorption, the vapor pressures reflect the composition of the liquid phase in equilibrium with the zeolite. From the gas chromatograph peaks, the $\alpha$EB/xylene isomer and $\alpha$Eb/desorbent factors were calculated.

TABLE 1

Changes in Selectivities with Desorbents for Various Beta Zeolites
Feed Equimolar $C_8$ Aromatics:Desorbent

| | eb px | eb mx | eb ox | eb Des | $C_8$:Desorbent (By Mole) |
|---|---|---|---|---|---|
| H-Beta | | | | | |
| No desorbent | 1.2 | 2.4 | 2.0 | — | — |
| Na-Beta | | | | | |
| No desorbent | 1.4 | 3.1 | 2.6 | — | — |
| p-diethylbenzene | 1.5 | 2.3 | 1.9 | 1.7 | 1:2 |
| K-Beta | | | | | |
| No desorbent | 1.6 | 5.2 | 4.3 | — | — |
| n-butylbenzene | 1.4 | 4.3 | 3.0 | 1.4 | 1:2 |
| Benzene | 1.6 | 2.8 | 5.2 | 0.9 | 1:3.2 |
| Toluene | 1.8 | 4.1 | 3.2 | 1.3 | 1:2 |
| p-diethylbenzene | 2.5 | 4.7 | 3.3 | 3.6 | 1:2 |
| Rb-Beta | | | | | |
| No desorbent | 2.0 | 7.4 | 5.2 | — | — |
| Benzene | 1.6 | 2.7 | 1.8 | 1.1 | 1:3.2 |
| Toluene | 1.7 | 4.9 | 3.6 | 2.2 | 1:2 |
| n-butylbenzene | 2.1 | 4.7 | 3.1 | 1.4 | 1:2 |
| n-pentylbenzene | 2.4 | 4.3 | 2.9 | 2.3 | 1:2 |
| Iodobenzene | 2.6 | 10.1 | 5.9 | 8.7 | 1:2 |
| p-diethylbenzene | 4.6 | 9.3 | 5.1 | 5.6 | 1:2 |

Table 1 shows the benzene and toluene as desorbents provide generally unacceptable selectivites for zeolite Beta. Substitution of the larger cations into the zeolite allows for enhanced selectivities with a number of desorbents. Paradiethylbenzene was clearly best in all cases.

EXAMPLE 2

An additional amount of zeolite Beta was produced as in Example 1. After calcining to remove the included organic ammonium template cation, one portion was exchanged with cesium chloride twice (with drying) to produce Cs-Beta I. Other methods of removing any such organic template would, of course, also be acceptable. A second portion was treated with the process described for Cs-Beta I, dried at 120° C., dried at 550° C. under flushing nitrogen, cooled and reexchanged twice at room temperature. The second portion is referred to as Cs-Beta II. A third and separate portion of the starting batch was treated in the manner described for Cs-Beta II and is referred to as Cs-Beta III.

Various desorbents were added to the zeolites in the method specified in Example 1. The resulting selectivities are shown in Table 2.

TABLE 2

Changes in Selectivities ($\alpha$) with Desorbents for Cs-Beta Zeolites
Feed Equimolar $C_8$ Aromatics:Desorbent

| | eb px | eb mx | eb ox | eb Des | $C_8$:Desorbent (By Mole) |
|---|---|---|---|---|---|
| Cs-Beta I | | | | | |
| No desorbent | 2.1 | 7.6 | 6.1 | — | — |
| Benzene | 2.0 | 3.0 | 2.4 | 0.6 | 1:3.2 |
| Toluene | 2.2 | 4.6 | 3.7 | 1.9 | 1:2 |
| n-butylbenzene | 2.4 | 4.3 | 3.3 | 1.8 | 1:2 |
| n-pentylbenzene | 2.4 | 3.9 | 3.0 | 1.8 | 1:2 |
| Iodobenzene | 2.5 | 7.7 | 5.0 | 4.9 | 1:2 |
| Cs-Beta II | | | | | |
| Prehnitene | 1.2 | 7.8 | 7.3 | 40.0 | 1:2 |
| o-diethylbenzene | 1.2 | 11.0 | 13.0 | 11.0 | 1:2 |
| Isodurene | 1.2 | 16.0 | 14.0 | 50.0 | 1:2 |
| n-dodecylbenzene | 2.0 | 6.1 | 4.3 | Not deter. | 1:2 |
| n-heptylbenzene | 2.7 | 4.8 | 3.9 | Not | 1:2 |

TABLE 2-continued

Changes in Selectivities (α) with
Desorbents for Cs-Beta Zeolites
Feed Equimolar C8 Aromatics:Desorbent

| | eb px | eb mx | eb ox | eb Des | C8:Desorbent (By Mole) |
|---|---|---|---|---|---|
| n-pentylbenzene | 2.8 | 5.2 | 3.7 | deter. 1.1 | 1:2 |
| n-nonylbenzene | 3.3 | 6.6 | 4.7 | Not deter. | 1:2 |
| Cs-Beta III | | | | | |
| No desorbent | 2.2 | 9.0 | 5.2 | — | — |
| o-methyl n-propylbenzene | 0.9 | 12.3 | 16.0 | 18.0 | 1:2 |
| m-diethylbenzene | 1.3 | 16.1 | 17.0 | 26.0 | 1:2 |
| Isobutylbenzene | 1.4 | 5.4 | 4.9 | 2.0 | 1:2 |
| p-methyl n-propylbenzene | 4.0 | 8.1 | 5.4 | 4.0 | 1:2 |
| p-diethylbenzene | 5.5 | 11.3 | 7.3 | 8.0 | 1:2 |

As in Example 1, monosubstituted benzenes and paradialkylbenzenes provide superior selectivities. If the differing processes for exchanging Cs into the zeolite gave different cation loadings, the differences in loading appear to result in only minor differences in performance.

EXAMPLE 3

This example compares the selectivities obtained by using the best desorbents of Examples 1 and 2 on zeolites which are outside the scope of this invention. Table 3 demonstrates about unique combinations of zeolite and desorbent result in enhanced selectivities.

TABLE 3

Effect of p-dialkylbenzenes on Various
Ethylbenzene Selective Zeolites
Feed Equimolar C8 Aromatics:Desorbent (1:2 by Mole)

| Zeolite | Desorbent | eb px | eb mx | eb ox | eb Desorbent |
|---|---|---|---|---|---|
| Rbx | paradiethylbenzene | 3.1 | 2.4 | 1.5 | 6.0 |
| CsX | paradiethylbenzene | 1.7 | 1.8 | 1.6 | 2.2 |
| CsX | para methyl n-propylbenzene | 3.6 | 3.9 | 2.3 | 9.0 |
| Rb-Beta | paradiethylbenzene | 4.6 | 9.3 | 5.1 | 5.6 |
| Cs-Beta | paradiethylbenzene | 5.5 | 11.3 | 7.3 | 8.0 |
| Cs-Beta | para methyl n-propylbenzene | 4.0 | 8.1 | 5.4 | 4.0 |

In summary, improved separation of ethyl benzene from isomeric mixtures of xylenes are possible by use of Beta zeolites in combination with certain desorbents.

I claim as my invention:

1. a process for the separation of ethylbenzene from a feedstream containing ethylbenzene and at least one xylene isomer comprising the steps of:
   (a) contacting the feedstream with a Beta zeolite under conditions suitable for adorbing ethylbenzene by the zeolite;
   (b) passing a desorbent selected from the group consisting of monosubstituted benzene wherein said substituent contains a heteroatom selected from the group consisting of O, S, P, and halogens, monoalkylbenzenes having from 3 to 12 carbon atoms in the monoalkyl substituent and paradialkylbenzenes through the zeolite during or after the contacting step, and
   (c) recovering a stream enhanced in ethylbenzene concentration from the zeolite.

2. The process of claim 1 wherein the substituent on the monosubstituted benzene desorbent is iodine.

3. The process of claim 1 wherein the desorbent is a paradialkylbenzene selected from the group consisting of paradiethylbenzene and paramethyl-n-propylbenzene.

4. The process of claim 3 wherein the desorbent is paradiethylbenzene.

5. The process of claim 1 wherein the feedstream contains orthoxylene, metaxylene, and paraxylene.

6. The process of claim 5 wherein the feedstream is substantially depleted in paraxylene.

7. The process at claim 1 wherein the zeolite contains at least one cation selected from the group consisting of alkali and alkaline earth metals and mixtures thereof.

8. The process of claim 7 wherein the zeolite contains Rb cations.

9. The process of claim 7 wherein the zeolite contains K cations.

10. The process of claim 7 wherein the zeolite contains Cs cations.

11. The process of claim 7 wherein the zeolite contains Na cations.

12. A process for the separation of ethylbenzene from a feedstream containing ethylbenzene and at least one xylene isomer comprising the steps of:
   (a) contacting the feedstream with an exchanged Beta zeolite under conditions suitable for adsorbing ethylbenzene by the zeolite,
   (b) passing a desorbent selected from the group consisting of n-butylbenzene, n-pentylbenzene, n-heptylbenzene, n-nonylbenzene, n-dodecylbenzene, iodobenzene, paradiethylbenzene, and paramethyl-n-propylbenzene through the zeolite during or after the contacting step,
   (c) recovering a stream enhanced in ethylbenzene content from the zeolite.

13. The process of claim 12 wherein the feedstream contains orthoxylene, metaxylene and paraxylene.

14. The process of claim 13 wherein the feedstream is substantially depleted in paraxylene.

15. The process of claim 12 wherein the zeolite contains at least one cation selected from the group consisting of alkali and alkaline earth metals and mixtures thereof.

16. The process of claim 15 wherein the zeolite contains Rb cations.

17. The process of claim 15 wherein the zeolite contains K cations.

18. The process of claim 15 wherein the zeolite contains Cs cations.

19. The process of claim 15 wherein the zeolite contains Na cations.

20. A process for the separation of ethylbenzene from a feedstream containing ethylbenzene and at least one xylene isomer comprising the steps of:
   (a) contacting the feedstream with a Beta zeolite containing Rb or Cs cations under conditions suitable for adsorbing ethylbenzene by the zeolite,
   (b) passing paradiethylbenzene through the zeolite during or after the contacted step, and
   (c) recovering a stream enhanced in ethylbenzene concentration from the zeolite.

21. The process of claim 20 wherein the feedstream contains orthoxylene, metaxylene and paraxylene.

22. The process of claim 21 wherein the feedstream is substantially depleted in paraxylene.

* * * * *